United States Patent [19]

Conners et al.

[11] Patent Number: 4,996,161
[45] Date of Patent: Feb. 26, 1991

[54] BREATH ALCOHOL TESTING SYSTEM

[75] Inventors: Patrick J. Conners, Montgomery; Lawrence R. Stevens, Mason; Don R. Gaiser, Dayton; Frank C. Pennypacker, Loveland, all of Ohio

[73] Assignee: Guardian Technologies, Inc., Denver, Colo.

[21] Appl. No.: 109,815

[22] Filed: Oct. 16, 1987

[51] Int. Cl.$^5$ .......................................... G01N 33/98
[52] U.S. Cl. .................................. 436/132; 128/719; 180/272; 340/573; 340/576; 422/84; 436/900
[58] Field of Search ................ 340/573, 576; 128/719; 73/23; 180/272; 250/343; 436/132, 900; 422/84, 85, 86

[56] References Cited

U.S. PATENT DOCUMENTS

| | | |
|---|---|---|
| Re. 29,008 | 10/1976 | Ott . |
| 3,525,811 | 8/1970 | Trice et al. ............................ 381/42 |
| 3,639,905 | 2/1972 | Yaida et al. ...................... 340/825.34 |
| 3,673,331 | 6/1972 | Hair et al. ............................ 381/42 |
| 3,809,067 | 5/1974 | Hoppesch ........................... 128/719 |
| 3,872,443 | 3/1975 | Ott . |
| 3,880,591 | 4/1975 | Burroughs ........................... 422/84 |
| 3,896,266 | 7/1975 | Waterbury . |
| 3,983,535 | 9/1976 | Herbst et al. ..................... 340/146.3 |
| 3,989,896 | 11/1976 | Reitboeck .............................. 179/1 |
| 3,990,436 | 11/1976 | Ott ..................................... 128/2 R |
| 4,048,986 | 9/1977 | Ott ..................................... 128/2 R |
| 4,093,945 | 6/1978 | Collier et al. ....................... 340/279 |
| 4,678,057 | 7/1987 | Elfman et al. ...................... 340/576 |
| 4,738,333 | 4/1988 | Collier et al. ....................... 340/576 |
| 4,749,553 | 6/1988 | Lopez et al. .......................... 422/84 |
| 4,843,377 | 6/1989 | Fuller et al. ......................... 128/719 |
| 4,868,545 | 9/1989 | Jones ..................................... 73/23 |
| 4,900,514 | 2/1990 | Fuller .................................... 422/84 |

FOREIGN PATENT DOCUMENTS

| | | |
|---|---|---|
| 0153883 | 4/1985 | United Kingdom . |
| 8702773 | 7/1987 | PCT Int'l Appl. . |
| 8707723 | 12/1987 | PCT Int'l Appl. . |
| 8614515 | 7/1986 | United Kingdom ................ 340/573 |

OTHER PUBLICATIONS

British Application 8614515, Jones (Lion Laboratories Limited).
"Voiceprint Identification" by L. G. Kersta of Bell Telephone Laboratories, Inc. published in Nature on Dec. 29, 1962.
Brochure: "Cherry Voice Scribe ® 1000 Speech Recognition System" Bulletin Number CE-1470.
Brochures Describing Fingermatrix–Product Data Sheet.
Advertisement entitled: "For People Who Understand the Risks and Don't Like the Odds" by Guardian Interlock Corporation.
Article entitled "VoiceKey ® Voice Verification Systems for Access Control" by Ecco Industries, Inc.
Article entitled: "Voxtron Voice-Controlled Access System Fulfills Needs for Sophisticated Security Protection" published by Voxtron Systems, Inc.

(List continued on next page.)

Primary Examiner—Robert J. Warden
Assistant Examiner—Timothy M. McMahon
Attorney, Agent, or Firm—Wood, Herron & Evans

[57] ABSTRACT

A breath alcohol testing system for advantageous use in unsupervised blood alcohol testing includes a face mask having for receiving a breath sample, components to confirm the identity and components to insure that this identity act and breath delivery are performed by the same person. The system requires that the face mask continuously engage the face of the subject between identity confirmation and breath delivery. By making the continuing physical presence of a subject an operative link in the system during both identity confirmation and breath delivery, the integrity of unsupervised testing is greatly enhanced.

27 Claims, 3 Drawing Sheets

OTHER PUBLICATIONS

Article entitled: "Ecco Unveils New Products & Sales": OEM Board to Debut in Home Confinement System: published Sep., 1987 in Personal Identification News.

Brochure entitled "Texas Instruments Ti-Speech ® System: Enhance the Value of Your Program with the Most Complete System Available" by Texas Instruments, Inc.

Advertisement for "On Guard System" by Hitek Community Control Corp.

Article entitled "New Devices May Keep Drunk Drivers Off Road" by Gregory W. Griggs, Dated Monday, Oct. 6, 1986.

Article entitled: "Fighting the War on Drunk Driving: Judges View Interlock Device Which Prevents Car From Starting" By Dale Gardner, The News Journal, Daytona Beach, Florida, Published Saturday, Oct. 18, 1986.

Publication Entitled "Electronic Monitoring and Correctional Policy: The Technology and Its Application" by Charles M. Friel, Joseph B. Vaughn and Rolando del Carmen, published by the United States Department of Justice in Jun., 1987.

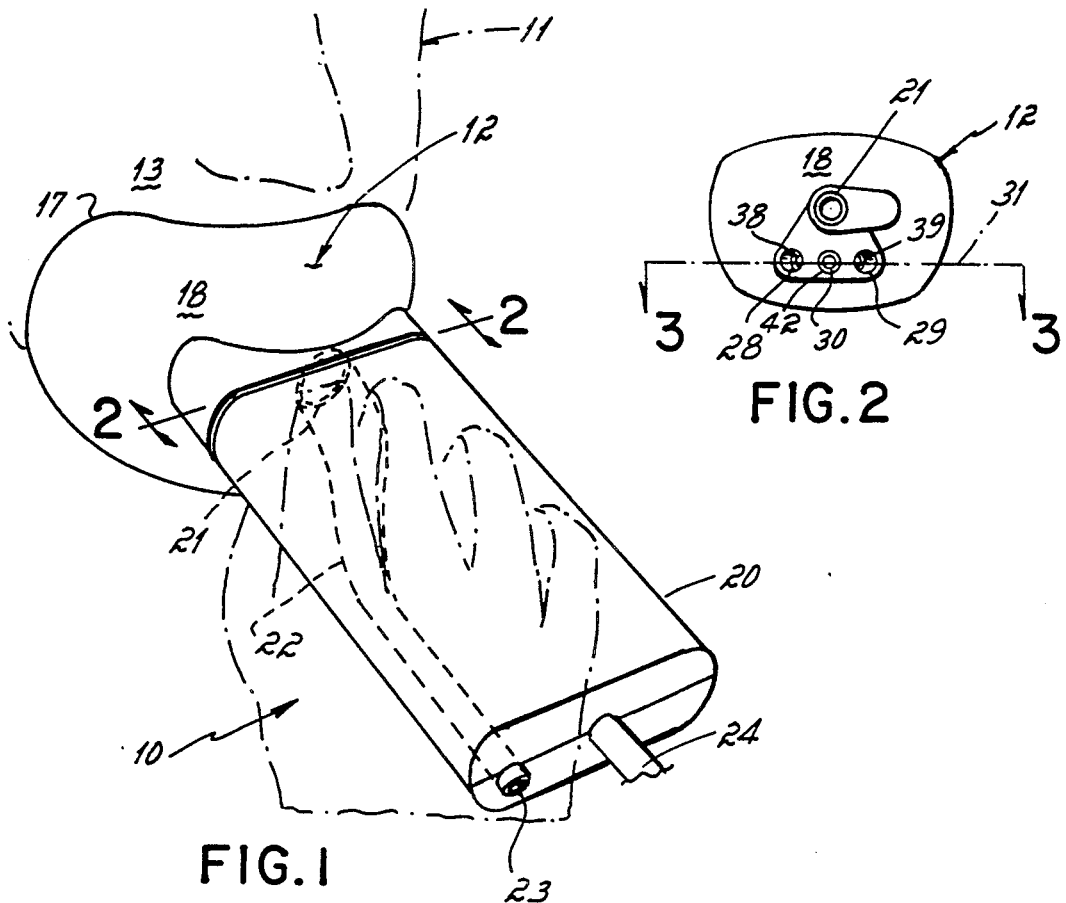
FIG. 1
FIG. 2
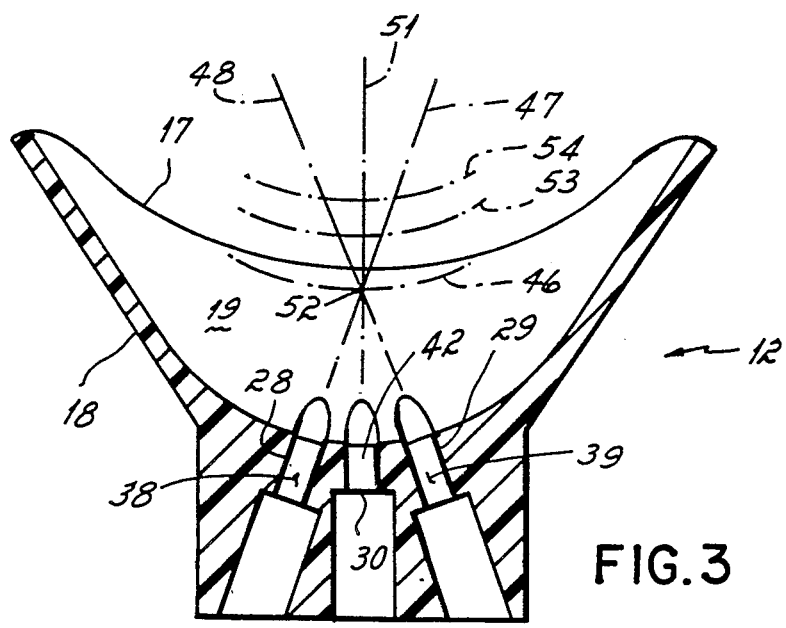
FIG. 3

BREATH ALCOHOL TESTING SYSTEM

Field of the Invention

The present invention relates generally to automatic systems for verifying the identity of a particular person, measuring breath alcohol concentration in a breath sample and verifying that the breath sample comes from the same person particularly when the identity verification and breath alcohol measurement are performed on a person with an incentive to falsify the results and when there is no one who will supervise the tests.

Background of the Invention

Breath alcohol testing systems operate according to the well known principle that the gas present in the alveoli of the lungs has an alcohol content directly proportional to that of the blood stream. The blood alcohol content (B.A.C.) of a subject can thus be accurately determined by obtaining a deep lung breath sample of the subject in a breath delivery apparatus for analysis by the testing system.

In many situations, the breath alcohol concentration test is administered to a subject under supervised conditions, and no danger exists as to the subject somehow delivering or presenting a bogus breath sample. A common example of a supervised breath alcohol concentration test occurs when a police officer administers the test to a subject suspected of operating a motor vehicle under the influence of alcohol. The police officer can easily verify the identity of the intended subject and the authenticity of the breath sample obtained. There are other applications for breath alcohol concentration tests, however, where direct supervision of the test subject is neither desired nor practical.

One such application is in a vehicle interlock system. Vehicle interlock systems, as they are commonly referred to, link an alcohol breath tester to the ignition system of a vehicle such as an automobile. They operate by requiring the user to pass a breath alcohol test before the user's vehicle can be started. Only the delivery of a breath sample with an alcohol content below a predetermined threshold level will enable the ignition system to start the user's engine. Such a system is described in U.S. Pat. No. 4,093,945 issued to Collier et al expressly incorporated herein by reference in its entirety. Another such system is described in applicant's pending patent application, entitled "Breath Analyzer Mouthpiece System," Ser. No. 07/045,827, filed on May 1, 1987, also expressly incorporated herein by reference in its entirety.

Conscientious drivers may install vehicle interlocks in their automobiles as a safety measure and use them voluntarily. On the other hand, the use of an interlock is frequently compelled to some degree. For example, a teen who borrows a family vehicle equipped with an interlock may not be a truly voluntary user. Moreover, the installation of a vehicle interlock is increasingly dictated by court order as a condition for allowing persons convicted of driving under the influence of alcohol to continue to drive.

Another case where breath testing may be performed without direct supervision and where attempts at evasion may be a problem is in a "home arrest" or remote confinement system wherein a prisoner is confined to a designated location and monitored from another location for compliance with behavioral restrictions including abstinence from substances such as alcohol. A growing number of states use home confinement for DWI offenders and pre-parole release programs. In either situation, any alcohol use is an imprisonable violation.

To monitor the location of a prisoner during home confinement, and his or her abstinence from the use of alcohol, common practice requires that an officer of the law make a house call at randomly selected times with a breath analysis testing system in hand. Although random house calls and breath tests of this sort have proved successful, the cost of this success has been dearly paid for in the form of substantial expenditures in time and manpower.

One such system for home confinement is disclosed in co-pending, commonly assigned U.S. patent application Serial No. 07/041,698 entitled "Remote Confinement System," filed on Apr. 21, 1987, which is expressly incorporated herein by reference in its entirety.

Whenever a breath analysis system is to be operated in unsupervised conditions, whether a vehicle interlock system, a home arrest system or any other system linked to a blood alcohol test, the opportunity exists for the user to attempt to circumvent or cheat the system by delivering or presenting a bogus sample to the tester in lieu of an actual breath sample. For example, a substitute sample may be attempted to be delivered by balloons or hoses attached or directed to the mouth of the tester. A test apparatus might erroneously analyze this gas as it would an authentic breath sample, and accept it as passing. Subjects may also attempt to circumvent the interlock by passing the breath sampling mouthpiece to an accomplice, who has not been drinking in excess, for breath sample delivery.

Other attempts to defeat alcohol breath tests involve the use of filters, such as charcoal filters, which tend to remove alcohol from the breath sample being delivered. Such attempts are made by placing a filter over the mouthpiece of the breath tester and then blowing through the filter into the mouthpiece. Some filters can remove enough alcohol from the breath sample entering the sampling tube to permit the breath test to be evaded by a prospective driver whose unfiltered breath exceeds the permissible alcohol limit.

Some prior breath alcohol testing systems provide countermeasures which require a confirmation of the identity of a subject as a necessary condition to delivery of an unsupervised breath sample. For example, a prior system requires that the subject keypunch a predetermined alphanumeric code into a controller in communication with the breath alcohol testing system in order to initiate the testing sequence. However, a subject can easily circumvent this countermeasure by simply divulging the alphanumeric code to an accomplice.

Another countermeasure for a breath alcohol testing system which is much more difficult to circumvent is described in detail in co-pending U.S. patent application Ser. No. 907,881, entitled "Sobriety Interlock With Unsupervised Confirmation Of Operator Identity" and filed on Sept. 15, 1987, which is expressly incorporated herein by reference in its entirety. In that system, a predetermined code is also entered into a controller, but the predetermined code is in the form of an identity confirming act performed by the intended subject. The designated test subject is trained to perform an identity-confirming act which is not readily learnable in fewer than a certain number of attempts. Successful performance of this act within a predetermined number of attempts confirms the identity of the subject and permits the breath test to be passed if the breath is below a specified alcohol limit. The system requires that at least a portion of the identity-confirming act, which preferably consists of a coded sequence of timed breath pulses and pauses, take place substantially contemporaneously with at least a portion of the delivery of the breath sample to be measured. Because the coded sequence of timed breath pulses and pauses is not easily learned within a predetermined number of attempts, this system frustrates attempts to circumvent the test by divulging to an accomplice the identity-confirming act. Moreover, the required substantially contemporaneous delivery of the breath sample after the intended subject has performed the identity confirming act, frustrates attempts by the identity confirmed subject to transfer or hand off the breath delivery apparatus for delivery of a bogus sample by the accomplice.

Although this system has proved successful in the field, and even though circumvention is unlikely, it might eventually be circumvented by extensively training an accomplice to successfully perform the identity confirmation act prior to delivery of a bogus sample. Moreover, trained individuals sometimes succeed in successfully transferring or handing off the delivery apparatus, even for extremely short periods of time between completion of the identity confirming conduct and the required delivery of the breath sample. Also, another disadvantage of such a system is that it requires expensive and time consuming set-up and training for those persons authorized or compelled to use the system.

Accordingly, it is an objective of the invention to provide an improved breath alcohol testing system having increased certainty in identity confirmation of an intended subject during unsupervised delivery of a breath sample to the system, and which prevents a person other than the one identified from supplying the breath sample.

It is a further objective of the invention to provide a breath alcohol testing apparatus which greatly reduces the training required to operate the system.

It is a further objective of the present invention to provide a breath alcohol testing system having countermeasures to prevent attempts to deliver a bogus breath sample during unsupervised breath alcohol testing.

It is yet a further objective of the present invention to provide a breath alcohol testing system that requires, in combination with a breath sample analysis, performance of an identity confirming act that cannot be taught to an accomplice.

It is still another objective of this invention to provide a breath alcohol testing system having a predetermined location for the delivery by a subject of a breath sample, and for the performance by the same subject of an identity confirming act.

Summary of the Invention

To these ends, a preferred embodiment of a breath alcohol testing system includes a face mask having breath sample receiving means, components of an identity confirming means, and components of means for insuring that this identity act and breath delivery are performed by the same person. More particularly, the system includes a voice analyzer module, a breath tester module, a microphone disposed within the face mask, an infrared light emitting diode and an infrared sensitive photo transistor in the face mask, and a breath receiving tube defined in the mask. The voice analyzer module requires delivery to the microphone of voiced words originating from a source closer to the microphone than the outer edge of the mask. A controller and user display are also provided.

In use, the mask is placed against the face of a subject who speaks predetermined words into the microphone for voice identity confirmation. Thereafter, a breath sample is delivered for testing. Alternatively, voice identity confirmation may take place after delivery of the breath sample. The mask defines a predetermined location for the delivery by the subject of a breath sample, and for the performance by the same subject of an identity confirming act.

During the voice and breath delivery process, a pulsed infrared beam from the light emitting diode is reflected from the subject's skin onto the photo transistor. In the absence of other light, a pulsed current is generated and analyzed to produce a logic signal to the controller, thus enabling the breath test to take place. The pulsing current is indicative of the continued existence of an operative link which includes the subject's presence in the mask. If the mask is moved from his face, either extraneous light is admitted, decreasing the sensed current, or the pulsations are eliminated since no infrared light is reflected by the subject's face. In either case, the logic signal to the controller switches to disable the breath testing module. Thus, the system detects the attempt to remove the mask for delivery of a bogus or substitute breath sample, and subsequently records the failure and terminates the test.

The voice analyzer requires a voice signal delivered to the microphone within the mask. If a reflective device is used in the mask as a substitute for the user's face, it will tend to block entrance of a user's mouth into the mask and a confirmable voice cannot be provided in the mask to the microphone. Defeat of removal detection is thus prevented. Accordingly, use of the mask insures that the person who delivers the voice sample for identity confirmation is the same person who delivers the breath sample. The mask cannot be handed off, nor removed for a bogus or substitute breath delivery.

By making the continuing physical presence of a person's face an operative link in the system during both identity confirmation and breath delivery, the integrity of unsupervised testing is greatly enhanced.

Also, operation of such an apparatus requires less training than certain prior systems while yet maintaining a very high degree of integrity. Voice analysis is not generally defeatable, yet delivery of certain words for identification is an easy task, readily learned and accomplished.

These and other objects and advantages of the present invention will be more readily apparent from the following detailed description of a preferred embodiment of the invention and from the drawings in which:

Brief Description of the Drawings

FIG. 1 is a perspective view of the face mask of this invention held in place against the lower portion of a human face;

FIG. 2 is an end view of the face mask taken generally along lines 2=2 of FIG. 1;

FIG. 3 is an enlarged cross-sectional view of the face mask of this invention, taken along lines 3—3 of FIG. 2;

Detailed Description of the Invention

Figure 4:
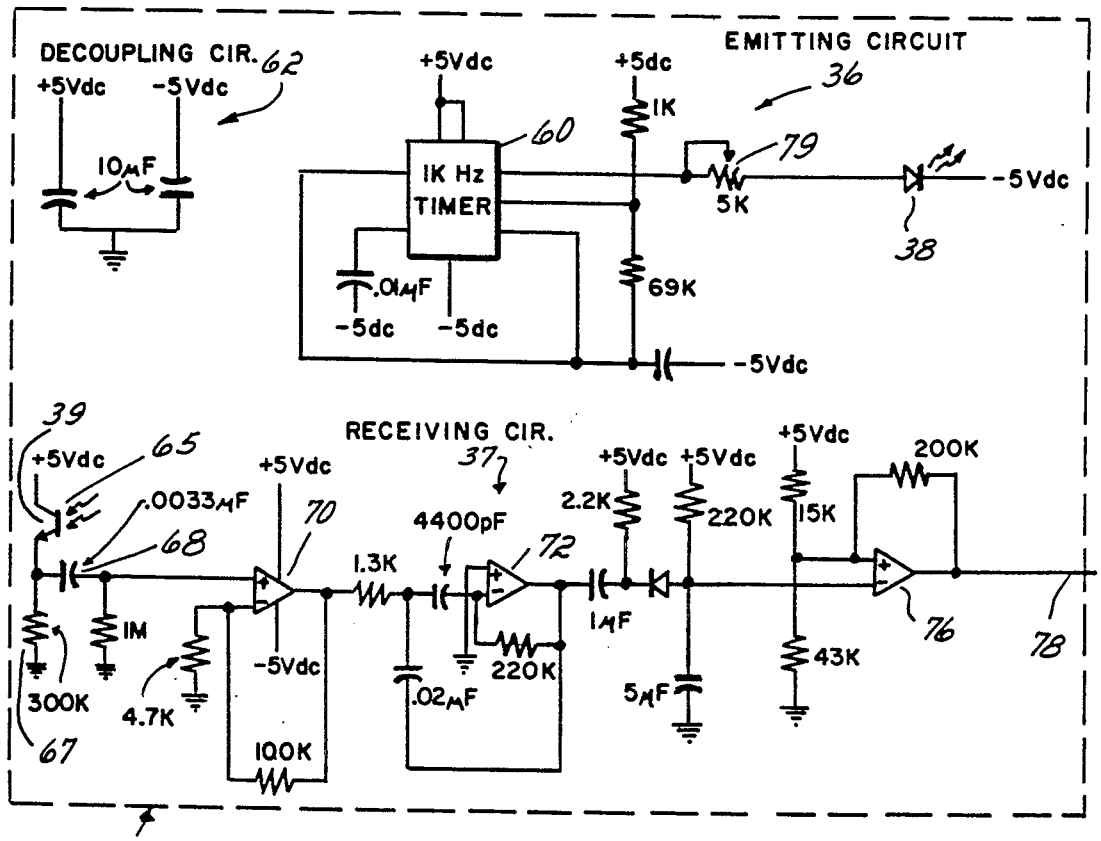
FIG. 4 is a schematic diagram showing the components of the anti-hand-off circuit.

This invention comprises a breath alcohol testing system 10 which provides increased certainty in identity confirmation of a subject 11 during unsupervised delivery of a breath sample to the system. The breath alcohol testing system 10 has countermeasures incorporated therein to detect any attempt to deliver a bogus or substitute breath sample to the testing system, in lieu of an actual breath sample of an intended subject. The blood alcohol testing system 10 of this invention is particularly advantageous in home arrest situations, but is equally adaptable to other applications such as vehicle interlock systems.

According to the invention, as shown in FIG. 1, a face mask 12 is adapted to engage the lower portion of the face 13 of the subject 11, enclosing the mouth, lips and a portion of the chin. The face mask 12 is preferably molded out of A.B.S. or polycarbonate, but may be molded out of urethane or any other suitable molding material. The face mask 12 is hollow and generally conical in shape, with a shaped edge 17 that arcuately recedes along top and bottom portions thereof to more completely engage and enclose and fit against the human face. Face mask 12 acts as a barrier to isolate the subject from outside interference during the breath alcohol test, and to provide darkness within the mask as desired for an anti-handoff means as will be described. Face mask 12 has an external surface 18 and an internal surface 19. External surface 18 converges away from edge 17 toward a handle 20 which houses some of the components of the breath alcohol testing system 10. Face mask 12 may be fixedly secured to handle 20, or adapted for removable attachment thereto.

Figure 5:
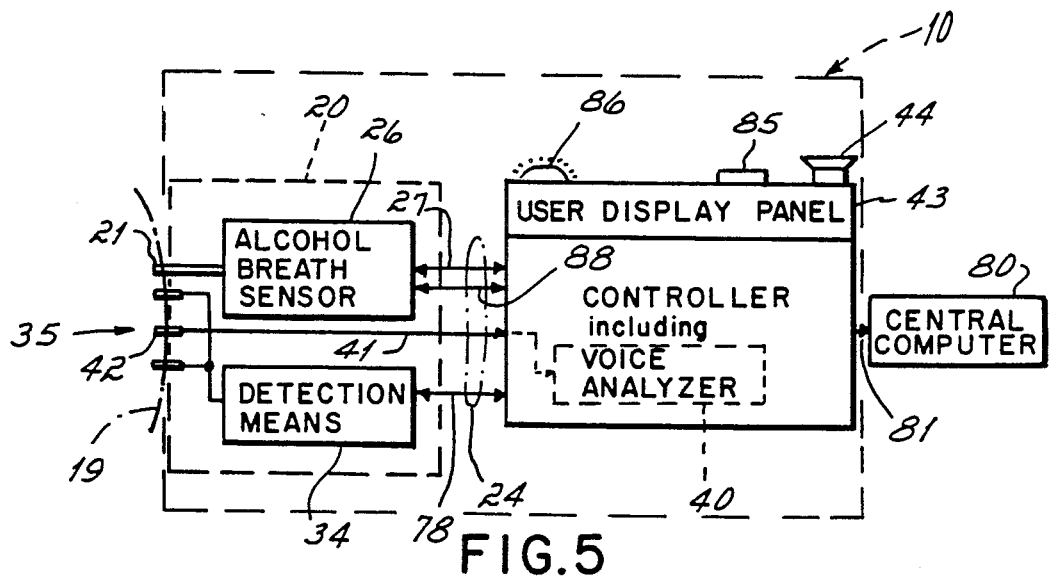
FIG. 5 is a block diagram of the breath alcohol testing system of this invention, showing the face mask, detection means and voice verification means incorporated therein.

Internal surface 19 converges toward, and defines, a breath tube 21 which receives the breath sample from subject 11 for conveyance through a breath test chamber 22 and thereafter through an exit, or exhaust, port 23. Alcohol sensing means 26 (see FIG. 5; not shown in FIG. 1) reside in communication with chamber 22 to generate an alcohol sensing signal that is correlated to the alcohol concentration in the breath sample passing through chamber 22. The alcohol sensing means includes an alcohol sensing device, preferably a semiconductor sensor such as Model TGS #813 manufactured by Figaro Engineering Company. Alternatively, Model TGS #812, also manufactured by Figaro Engineering Company, would be suitable. The signal from sensing means 26 is relayed via an electrical conductor 27 to a controller 25. Conductor 27 is encased by a protective connecting cable 24 which extends from the handle 20 to the controller 25. The controller 25 may be any type of microprocessor and associated circuitry, but is preferably of the 8086 type. Either a Motorola 6800 or an Intel 8051 would be sufficient for the purposes of the invention. If desired, an adapter may also be used to extend breath tube 21 to prevent saliva from entering test chamber 22 during delivery of the breath sample.

FIG. 2 shows an end view of the face mask 12, with the breath tube 21 located centrally therein. Internal surface 19 further defines three recesses, 28, 29 and 30 aligned along a horizontal (as viewed in FIG. 2) axis 31. The recesses are preferably located proximate the breath tube 21 in order to maximize accuracy in assuring identity confirmation of the subject during the breath alcohol test. Although FIG. 2 shows the recesses located below breath tube 21, they may be located elsewhere within internal surface 19. Detection or anti-handoff means 34, and identity confirmation means 35 are at least partially disposed within the face mask 12, residing within recesses 28 and 29 and 30, respectively.

When face mask 12 is placed against a human face, the detection means 34 provides a binary signal to the controller 25 to enable the test sequence to begin. Receipt of the enabling signal by the controller 25 is a necessary condition to the subject's performance of an identity confirming test and is also required until delivery of an unsupervised breath sample into the breath tube 21 has been completed. In other words, the continued physical presence of the subject forms an operative link between identity confirmation and unsupervised delivery of the breath sample. Any interruption of the enabling signal shuts down the breath alcohol testing system, thus, resulting in failure of the test. Thus, a transfer or hand off of the face mask by an identity confirmed subject to an accomplice in order to provide a bogus breath sample will be deterred, or at the very least, result in a failing of the breath alcohol test. The enabling signal is preferably provided in the form of a digital logic signal from detection means 34 to the controller 25. However, a mechanical latch which is set upon initial engagement of the face mask 12, and which unlatches upon pulling the mask away from the face 13, may be used to perform the same function.

Detection means 34, or means for insuring an operative link, comprises an emitting circuit 36 which emits pulsed signals at a known frequency in an outward direction from the internal surface 19 of the face mask 12 when the subject 11 initiates the test sequence (described in detail later). Although various types of pulsed signals, i.e. electromagnetic or even sonic waves, could be utilized to provide means for detection, the emitting circuit 36 preferably has an infrared light emitting diode 38 residing at least partially within recess 28 to emit pulses of infrared light at a frequency of about 1000 Hz. A receiving circuit 37 receives and detects the pulsed signals that have been reflected off an object proximate internal surface 19. Preferably, receiving circuit 37 comprises an infrared sensitive phototransistor 39 which resides at least partially within recess 29. The phototransistor 39 generates a signal to the receiving circuit 37. The signal is processed, and relayed to the controller 25, which provides an indication of the position of the face 13 with respect to the face mask. When the subject 11 has facially engaged face mask 12, the phototransistor 39 will receive the infrared pulses after they have been reflected off of the face 13 of the subject 11 and back toward internal surface 19. The detection means or anti-handoff means 34 is disclosed in greater detail below.

Although the breath alcohol testing system 10 of this invention can be adapted to work with any one of a number of identity confirmation tests, it is preferred that identity confirmation means 35 be performed by voice verification. Identity confirmation by voice verification is disclosed in U.S. Pat. No. 3,673,331, entitled "Identity Verification by Voice Signals in the Frequency Domain," issued in the name of George D. Hair and Jones U. Kincaid on June 27, 1972, and expressly incorporated herein by reference in its entirety. Voice verification enables identity confirmation of the subject with a high degree of accuracy because the voice characteristics of an individual provide a unique "fingerprint" which can be stored in memory and later recalled for comparison and analysis. Unlike other means for identity confirmation which have been incorporated into breath alcohol testing systems, voice verification depends upon the inherent voice characteristics of the individual, and are not easily imitated to obtain identity confirmation of someone other than the intended subject.

Voice verification systems require a microphone to convert words spoken by a subject into electrical signals for recording and memory storage during an enrollment procedure and subsequently, during testing, for analysis and comparison with words previously spoken and stored in memory. Both the enrollment mode and the test mode require that a subject speak a number of predetermined words into a microphone. The subject is generally cued as to when to begin speaking by a "prompt" signal, which can be an audible signal emitted from a loudspeaker in communication with the voice verification system.

During enrollment, which is carried out under direct supervision, the subject is prompted to recite into the microphone a number of preselected words as they are emitted from the loudspeaker. The voice verification system stores data related to various aspects or characteristics of the subject's speaking voice. At a later point in time, the subject will be prompted to again recite the same words in a randomly selected order. In order to confirm the identity of the subject, various aspects of the words spoken must match those stored in memory.

Preferably, identity confirmation means 35 is provided by voice verification means comprising voice analyzer 40 housed adjacent controller 25, a microphone 42 disposed within recess 30 and an electrical conductor 41 which provides communication of electrical signals therebetween. One particular voice analyzer 40 or voice module that may be used is supplied by Ecco Industries under the trademark VoicePac. VoicePac is a half-card with 16 bit CMOS 8088 processor. Conductor 41 resides within cable 24. If desired, circuitry may be added within handle 20 to preamplify the signal generated by microphone 42 before it is conveyed via line 41 to voice analyzer 40. A control panel 43 mounted to controller 25 provides a loudspeaker 44 in communication with the voice analyzer 40. The loudspeaker 44 provides the "prompt" signal used during both enrollment and testing. However, indicating lights or other prompting means could be used.

Before providing a narrative of the sequence of events which must occur in order for a subject to pass the breath alcohol test administered by the system 10 of this invention, a full appreciation of this invention requires further description of the relative positioning of the microphone 42, the light emitting diode 38, the phototransistor 39, and a chin portion 46 of the subject 11 when the face mask 12 resides in engagement with the face.

The face mask 12 acts as a barrier to isolate the microphone 42 from outside noise which might otherwise interfere with or possibly circumvent voice verification. The shape of the mask 12 also places the microphone 42 in an accurately repeatable position relative to the person's mouth, a requirement for accurate voice verification of the subject 11. If the relative position of the microphone varies with respect to the subject's mouth, voice characteristics of the subject will likewise vary and the accuracy of voice verification is diminished. In other words, if the original voice samples obtained during the enrollment mode were taken with the face mask 12 held against the face 13 and enclosing the mouth, the lips and a portion of the chin 46, the voice sample will be accurately repeatable and the voice analyzer 40 can be adapted to reject voice samples that deviate even a small degree from the originals. Therefore, the subject 11 must hold the face mask 12 in about the same location during the testing mode in order to pass the identity confirmation test. Variation of the relative position of the face by as little as $\frac{1}{2}''$ will usually cause voice distortion that results in failing the test. Thus, the use of the face mask 12 facilitates the use of the high accuracy voice analyzer 40 described earlier, which is not easily defeatable by providing voice samples from a miniature speaker within the facemask or by otherwise projecting the voice sample from outside of the mask. The use of high accuracy voice analysis provides a greater degree of certainty in identity confirmation while the detection means 34 provide an operative link between identity confirmation and breath delivery, thus resulting in increased accuracy in the results obtained during unsupervised breath alcohol testing.

FIG. 3 shows the relative position of the infrared light emitting diode 38, the infrared sensitive phototransistor 39 and the microphone 42, residing within recesses 28, 29 and 30, respectively. In this view, the chin 46 appears below the bottom portion of edge 17, indicating that the face 13 is within the face mask 12. This provides voiced delivery of words from a source closer to the microphone 42 than the outer edge 17 of the mask. The light emitting diode 38 and the phototransistor 39 have direction lines 47 and 48, respectively, which are angled inwardly to intersect a vertical (as shown in FIG. 3) axis 51 through microphone 42 at an intersection point 52, which lies approximately $\frac{3}{4}''$ away from the internal surface 19. With the face mask 12 properly engaging the face, the chin 46 will reside at this intersection point 52. Thus, the phototransistor 39 receives maximum exposure to the infrared pulses that are reflected off of the chin 46. Both the infrared light emitting diode 38 and the phototransistor 39 have built in lenses that focus the light. The sensitivity of the phototransistor 39 is reduced to about half maximum for light coming in at 10 degrees from the center and further reduced for greater angles. The light intensity of the infrared light emitting diode 38 is reduced to about half maximum for light radiated at 10 degrees from the center and further reduced for greater angles. The reception of pulsed light off the subject's chin is maximized when the chin 46 of subject 11 is located at the intersection 52 of direction lines 47 and 48. When the face mask 12 is moved away from the face, or vice versa, a relative location such as designated by either arc 53 or arc 54, the signals are directed to one side of axis 51 while the phototransistor 28 is aimed at the other side. Thus, the amount of pulsating light received by the phototransistor 39 rapidly diminishes both due to the increased distance and due to the increased amount of misaiming.

The infrared light emitting diode 38 and the phototransistor 39 are connected to an emitting or directing circuit 36, and a receiving circuit 37, respectively, which are shown in FIG. 4. Detection means 34 comprises directing circuit 36 components, receiving circuit 37 components and the components of a decoupling circuit 62, all of which are shown in FIG. 4. These three circuits are preferably mounted within handle 20.

Power is supplied via power lines (not shown) residing within cable 24. Advantageous results have been achieved using +5.0 volts and −5.0 volts, to provide a voltage swing of 10 volts. Other voltages would also work. The emitting circuit 36 generates pulses of infrared light having a frequency of about 1000 Hz. Higher or lower frequencies would also work, but it is important to avoid frequencies near 60 Hz and 120 Hz since electric lights and television sets working off 60 Hz power produce light strongly modulated at these frequencies. If the power frequency is 50 Hz, then 50 and 100 Hz are to be avoided. An oscillator or timer 60 produces the 1000 Hz pulses. The oscillator 60 is preferably a type 555 integrated circuit that is available from either Motorola or NEC. Because use of a 555 type integrated circuit may result in the generation of current pulses which couple to the rest of the circuit through power lines to cause interference with detection, a decoupling circuit 62, also shown in FIG. 4, may be added to the detection means 34. The infrared light emitting diode 38 can be a gallium arsenide device, for instance a MLED930 manufactured by Motorola.

The phototransistor 39 is an infrared sensitive device, for instance an MRD370 manufactured by Motorola. Note that the base of the phototransistor 39 is not connected since the input current is generated by light falling on a semiconductor junction 65. Note also that type MRD370 is a Darlington type phototransistor; single junction transistors or photodiodes could be used if additional gain is provided.

The receiving circuit 37, shown in the lower portion of FIG. 4, provides means for receiving or monitoring pulsed signals that have been reflected off of face 13 and back toward internal surface 19. The receiving circuit 37 also detects light from outside the face mask 12. A resistor 67 and a capacitor 68 are connected to the emitter portion of the phototransistor 39. If the face mask 12 is held against the face, 13 the pulsed current through the phototransistor 39 will be less than about 25 microamperes, resulting in a voltage drop across resistor 67 of about 7.5 volts. The voltage across the resistor 67 will contain a periodic component of about 0.05 volts at the frequency of the impulses. Other voltage components will also result, due to noise and small amounts of background light. The varying components are coupled by capacitor 68 into an operational amplifier 70, one section of a JFET input operational amplifier, type MC34004 (manufactured by Motorola), which operates as a buffer that will provide some amplification as well as a low source impedance to drive an operational amplifier 72. Operational amplifier 72 can be another section of a MC34004. Its associated resistors and capacitors provide an active band pass filter designed to pass 1 kHz signals. The active filter amplifies the 1 kHz signal while rejecting other signals. The amplified 1 kHz signal from operational amplifier 72 is rectified by a diode 74 and its associated resistors and capacitors before being coupled to the negative input terminal of an operational amplifier, 76, another section of a MC34004, which acts as a Schmitt trigger to provide a digital logic signal to the controller 25 via an electrical conductor 78 which resides within cable 24. The Schmitt trigger is biased to provide a voltage swing of about 9 volts, from about −4.5 volts to about +4.5 volts. If there is little or no 1 kHz signal at the output of operational amplifier 72, the input to the Schmitt trigger is high, due to the resistors connected to the power supply positive. A high input to Schmitt trigger 76 results in a low output. When the face mask 12 engages the face, the pulsed voltage drop across resistor 67 produces a low input to the Schmitt trigger 76, causing the output to swing high. A "high" signal from operational amplifier 76 to controller 25 indicates that the face mask is in engagement with the face. A "low" signal indicates otherwise, that pulsed signals of about 1000 Hz are not being received by phototransistor 39.

If the face mask 12 is not held against the face 13 and internal surface 19 is exposed to even moderate light, (greater than 1/2000th of outside illumination on a clear day), the phototransistor 39 will receive the ambient light and produce a current that will be limited by the resistor 67. The capacitor 68 connected between the phototransistor 39 and the positive terminal of the operation amplifier 70 will block d.c. current resulting from direct light falling upon junction 65. Unwanted voltage variations amplified by operational amplifier 70 will be blocked by operational amplifier 72, which only passes signals having a frequency of about 1000 Hz, that of the emitted pulses. Until the face mask 12 is placed in engagement with the face, the output of operational amplifier 76 will be low, indicating to the controller the absence of an enabling signal.

Under dimly lit conditions, with neither direct light nor reflected infrared pulses hitting junction 65, no signal is amplified by operational amplifier 70 and the output to controller 25 remains low. Thus, an enabling signal to the controller 25, can only be attained by reflecting or directing infrared pulses of 1000 Hz toward junction 65 of phototransistor 39. Moreover, attempts to reflect the pulsed signals off an object other than the face, will place the reflecting object in a position which blocks access to the microphone 42, thus causing voice distortion that results in a failed test.

Adjustment of the intensity or amplitude of the pulsed infrared signals transmitted by the light emitting diode 38 may be required, depending among other things upon the skin complexion and facial hair characteristics of the individual to be tested. An individual having a rather fair complexion will reflect the signals more efficiently than someone having a darker complexion. Also, a face with no facial hair reflects the pulses more efficiently than one having a beard. Intensity can be varied by varying the resistance of a variable resistor 79 in the emitting circuit 36.

There are other possible configurations or alternatives for providing the function of detection means 34. One possibility is to use a separate circuit to measure total average light instead of using current saturation to detect excessive light. This allows greater sensitivity, but at the cost of greater circuit complexity. If a separate circuit is used, it is possible to incorporate a differentiator; this makes the circuit more sensitive to changes that would result if the person being tested moved the mask. Another possibility contemplates the use of pulsed sound signals having a frequency on the order of 100 kHz.

The security of the system can also be further enhanced by reducing elapsed time between the subject's completion of the voice verification test and when he or she starts to blow for the alcohol breath test. Measurements have shown that most sober people can start to blow within 0.5 seconds after a prompt. By allowing no more than 0.5 seconds, it becomes more difficult to pass the device to an accomplice in addition to the other countermeasures. If attempts are made to defeat the system by working in the dark, using devices to reflect the pulsating light and handing the mask back and forth, the limited time span further reduces the chance of successful circumvention of the test.

With the blood alcohol testing system 10 of this invention placed in the home of a subject, his or her abstinence from the use of alcohol can be accurately monitored and recorded at a centrally located computer 80 connected to the controller 25 by connector means 81, which can be a telephone line. By cross referencing the subject's work schedule, and perhaps his or her sleeping hours, the central computer 80 is programmed to select points either randomly or fixed in time during which the subject is required by court order to remain at home. At each test time, a call signal over cable 81 to controller 25 activates an alarm at the subject's residence. The alarm is preferably an audible summons signal over loudspeaker 44. Preferably, the controller 25 may have an internal clock to automatically test according to the subject's schedule, with the results subsequently conveyed to the computer 80.

Figure 6:
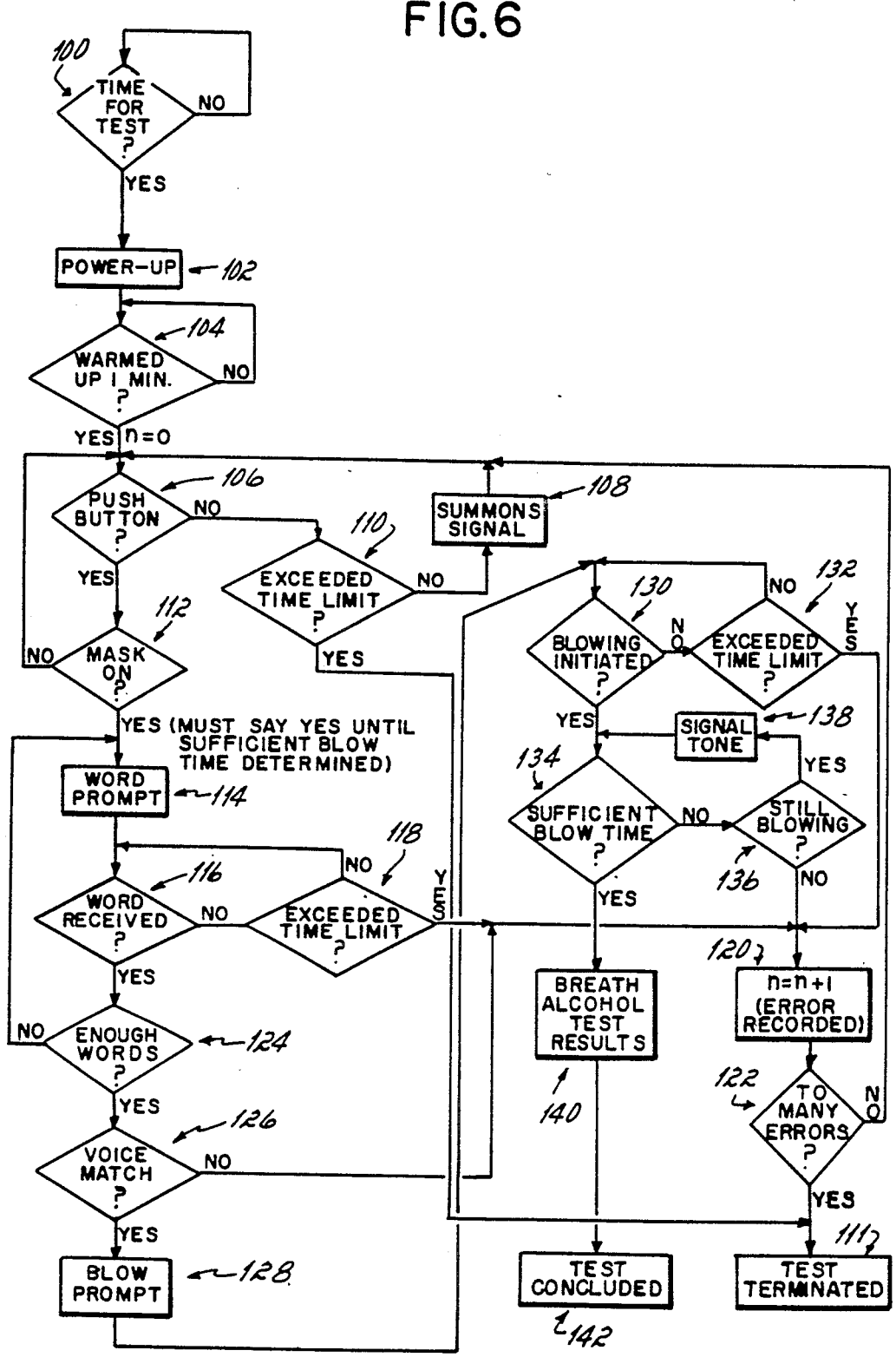
FIG. 6 is a flow chart depicting the sequence of operation of the breath alcohol testing system of this invention.

FIG. 6 provides a flow chart depicting the sequence of operation for the breath alcohol test. A description of this sequence requires reference to both FIG. 5, with the appropriate components and connections labelled, and FIG. 6, with numerals indicating each "decision" or "signal" provided to or from the controller 25 or the voice analyzer 40 during the test.

At a time for the subject 11 to be tested, decision 100, the controller 25 initiates the steps necessary to carry out a breath alcohol test. Alternatively, a signal from main computer 80 at a remote location is communicated via cable 81 to the controller 25 located in the subject's house. The decision 100 indicates that it is time to activate or supply power to the breath alcohol testing system 10. A power up signal is indicated at 102. The controller 25 decides whether or not sufficient warming up has taken place, decision 104. After a warm up period of about one minute, required to purge the impurities from the testing chamber 22, the controller 25 determines whether or not the subject 11 is ready, decision 106. A "ready" decision is conveyed to the controller 25 by depression of a pushbutton 85 mounted to the user panel 43, of controller 25. Until the pushbutton 85 is depressed, decision 106, the controller emits a summons signal, signal 108, through the loudspeaker 44 mounted to panel 43. After a period of time approximately five minutes in duration, decision 110, the failure to depress the pushbutton 85 will indicate to the controller 25 that the test has been terminated, decision 111. The termination decision is relayed from the controller 25 to the main computer 80 to indicate that the subject 11 has failed to respond, possibly signifying a violation of the home arrest restrictions.

Once the pushbutton 85 has been depressed, further participation requires that the subject 11 facially engage the face mask 12 to provide the enabling signal to the controller 25, decision 112. If the face mask 12 is not on, the subject 11 must again depress the pushbutton 85 to initialize the test, indicating a return to decision 106 in FIG. 6. Although engagement of face mask 12, decision 112, is not actually required until after depression of the pushbutton 85, decision 106, the time lapse between decisions is a few microseconds. Because humans simply cannot react within this time sequence, the subject will actually be required to have the face mask 12 in place before depressing button 85, otherwise he or she will have to press button 85 a second time.

Once the controller 25 receives the enabling signal from line 78 of the receiving circuit 37, voice verification is ready to take place. Note that FIG. 6 indicates that a "yes" signal as to decision 112 must be received continuously until sufficient blow time has been determined, or in other words, until the subject 11 has completed delivery of the breath sample. Upon receiving the enabling signal, the controller 25 signals the voice analyzer 40 to randomly select one of the enrollment words, which is then audibly reproduced out of the loud speaker 44, signal 114. Alternatively, signal 114 may be provided by randomly lighting indicating lights located adjacent printed words on panel 43. The word prompt indicates to the subject 11 that the selected word is to be spoken into the microphone 42. If the subject 11 does not repeat the announced word, or, more appropriately, if the microphone 42 does not receive the word and transmit it to the voice analyzer 40, decision 116, the voice analyzer 40 will determine if a specified time limit for response has been exceeded, decision 118. If the time limit is exceeded, the voice analyzer 40 signals to the controller 25 to record an error, signal 120, for addition to a sequential error counter in the controller 25. Each time an additional error is counted, the controller 25 determines whether or not the subject has exceeded a predetermined number of allowable errors, decision 122. If he or she has, the test is terminated, signal 111. If he or she has not, the subject 11 may restart the test by depressing the pushbutton 85. The number of errors allowed can be varied according to the subject. If the word is correctly recited by the subject 11, voice analyzer 40 will next determine whether or not a sufficient number of words for accurate voice verification have been recited, decision 124. When a sufficient number of words have been recited, the voice analyzer 40 provides an indication to the controller 25 as to whether or not the identity of the subject 11 has been confirmed, decision 126. If a "negative" signal indicating no identity confirmation is received by the controller 25, an error is tallied, signal 120, and the controller 25 determines whether or not the predetermined number of errors has been exceeded, decision 122. By allowing a finite number of errors before failing the voice match test, the probability of a mistake being made by the voice analyzer 40 is significantly reduced. For example, if the voice analyzer 40 has an accuracy percentage of 98%, and the controller 25 is programmed to allow three errors, the probability of the voice analyzer 40 mistakenly failing to identify an intended subject three times in a row is 0.0008%.

If a "positive" signal indicating identity confirmation is received by the controller 25, a signal activates a blow prompt indicator 86, preferably an indicating light mounted on panel 43, to indicate to the subject 11 that he or she is to deliver a breath sample into the breath tube 21, signal 128.

Once the indicating light 86 has been activated, the subject 11 has approximately 0.5 seconds to commence delivery of the breath sample into breath tube 21, decision 130. Blowing is sensed by a pressure switch (not shown), which is mounted for communication with chamber 22 and generates a signal correlating to the pressure in the chamber 22. The signal is relayed to the controller 25 via an electrical conductor 88, which resides within cable 24. One particular pressure switch that may be used is supplied by Fairchild, Model #PSF100A. If blowing has not started within about 0.5 seconds, decision 132, a signal to the controller 25 indicates that another error is to be tallied, signal 120. Once blowing has started, the controller 25 determines whether or not blowing has continued for a sufficient duration of time, decision 134. The controller 25 then determines whether or not the subject has stopped blowing while he or she was still required to blow, decision 136. If sufficient blow time has not elapsed, and blowing is continuing, a tone is produced out of the loudspeaker 44, signal 138. If blowing has stopped before sufficient blow time has elapsed, another error is tallied, signal 120. After about four to five seconds have elapsed, the time required to convey a deep breath sample through the breath tube 21, past chamber 22 and out exit port 23, an analysis of the alcohol content of the breath sample will take place. The controller 25 receives the results of the test and then transmits them to the central operating computer 80 over cable 81, signal 140, where results are monitored and recorded over a period of time. The test is then terminated, for the time being, decision 142. If the subject "passes" the test, he or she has complied with home arrest restrictions. If the subject "fails" the test, a violation of home arrest conditions can be recorded and acted upon.

If the breath alcohol testing system 10 of this invention is used for a vehicle interlock system, the conclusion of the test provides either a positive signal to indicate a "pass" of the test and allow an automobile engine to be started, or a negative signal to indicate a "failure" of the test and prevent starting of the engine for a period of time. The alcohol sensing device 26 can be adjusted to allow a variable breath alcohol content to "pass" the breath alcohol testing system 10 of this invention. Such adjustment would be necessary in a vehicle interlock system, where a driver is not required to completely abstain from the use of alcohol, but is required only to have an alcohol blood content below a legally recognized limit.

In addition to home arrest and vehicle interlock, the invention as described can be adapted to a variety of uses and alternative functions. For example, to insure against possible loss of life or property, an owner of heavy machinery or any other type of manufacturing equipment may choose to require an operator to pass a breath alcohol test as a precondition to operation of the equipment. Under these circumstances, the breath alcohol test would most likely be unsupervised and there could be an incentive to cheat the test. The breath alcohol testing system of this invention could be easily adapted to insure that equipment is operated by an authorized individual and that the authorized individual has not been using alcohol.

Although this disclosure recites a breath alcohol testing system in which identity confirmation acts as a precondition to delivery of the breath sample, it is to be understood that, alternatively, identity confirmation could be required subsequent to delivery of the breath sample, so long as the detection means provides an operative link which effectively insures that the identity act and breath delivery are performed by the same person.

Furthermore, the controller 25 may be programmed to allow the subject a greater or lesser number of errors or alternatively, to weigh the errors differently. For example, a failure to recite the "prompted" word may be tallied on a separate counter from a failure to blow for sufficient duration. These minor modifications are a matter of preference and can be programmed into the controller 25 according to the particular circumstances requiring the use of a breath alcohol testing system.

While the above description constitutes a preferred embodiment of the breath alcohol testing system of this invention, various other alternative embodiments will be readily apparent to a person skilled in the art without departing from the scope of the invention. Accordingly, it is to be understood that applicant is to be bound only by the claims appended hereto.

I claim:

1. A breath alcohol testing system particularly suitable for unsupervised breath alcohol testing of a subject comprising:

a face mask having an internal surface, an external surface and an edge therebetween, said internal surface further defining a breath tube to convey a breath sample to means for testing said sample, said edge shaped for at least partially enclosing a portion of the face of a subject during delivery of said breath sample into said breath tube;

means responsive to the performance of an identity confirming act performed by said subject to verify the identity of said subject, said performance responsive means at least partially disposed within said face mask; and means partially disposed in said face mask for insuring that the same subject performs both said confirming act and said delivery of said breath sample wherein said insuring means monitors the location of the face with respect to the mask.

2. A breath alcohol testing system as in claim 1 wherein said insuring means monitors the continued physical presence of said subject within said face mask during the performance of said identity confirming act and during delivery of said breath sample to said breath tube.

3. A breath alcohol testing system as in claim 1 wherein said insuring means further comprises:

means for directing pulsed signals outwardly from said internal surface toward the face of said subject when said subject is in the proximity of said face mask; and means for receiving said directed signals reflected from said subject's face when said subject is in the proximity of said face mask, said receiving means generating a signal indicative of the continued position of said subject's face with respect to the face mask.

4. A breath alcohol testing system as in claim 3 wherein said directing means directs pulsed electromagnetic signals and said receiving means receives reflected, pulsed, electromagnetic signals.

5. A breath alcohol testing system as in claim 4 wherein said directing means emits pulsed infrared light and said receiving means comprises an infrared sensitive phototransistor that receives said pulsed infrared light reflected from said subject's face.

6. A breath alcohol testing system as in claim 1 wherein said internal surface further defines a voice receiving recess and wherein said performance responsive means further comprises:

a microphone residing within said recess; and voice verification apparatus in communication with said microphone to receive voiced samples from said microphone for comparison with prior recorded samples from said subject to verify the identity of said subject.

7. A breath alcohol testing system as in claim 6 wherein said voice verification apparatus requires voiced samples emanating from a source closer to said microphone than said edge of said face mask in order to verify the identity of said subject.

8. A breath alcohol testing system as in claim 7 wherein said internal surface further defines two recesses located on opposite sides of said voice receiving recess, and wherein said insuring means further comprises:
   means partially disposed within a first of said two recesses for directing pulsed signals outwardly from said internal surface toward the face of said subject when said subject is in the proximity of said face mask; and
   means partially disposed within a second of said two recesses for receiving said directed signals reflected from said subject's face when said subject is in the presence of said face mask, said receiving means generating a signal indicative of the continued position of said subject's face with respect to the face mask.

9. A breath alcohol testing system as in claim 1 wherein said face mask has a conical shape for enclosing the mouth, upper lip and chin of said subject during delivery of said breath sample to said testing system.

10. A method for unsupervised testing of an alcohol sample received from a predetermined subject delivering a breath alcohol test sample into a face mask, the method comprising the steps of:
    comparing a voiced sample delivered within said face mask with prior recorded signals stored in a voice analysis apparatus;
    confirming the identity of said subject as a necessary condition to the delivery of a breath sample;
    receiving within a face mask a breath sample to be analyzed by a breath sensing apparatus;
    monitoring the position of said face mask with respect to said subject to insure that said voiced samples and said breath sample emanate from said subject during continued presence of said subject within said face mask.

11. A breath alcohol testing apparatus particularly suitable for unsupervised breath alcohol testing of a subject comprising:
    means defining a predetermined location for the delivery by a subject of a breath sample, and for the performance by the same subject of an identity confirming act;
    a breath sample receiving passageway having a breath receiving port disposed within said location defining means;
    means disposed within said location defining means for confirming the performance of said identity confirming act; and
    means for monitoring the continued position of a subject within said predetermined location for confirming that the subject who performs said identity confirming act is the same subject who delivers said breath sample.

12. A breach alcohol testing system particularly suitable for unsupervised blood alcohol testing of a subject comprising:
    means for receiving a breath sample from a subject in order to determine a blood alcohol level;
    a face mask partially housing said receiving means, the face mask engaging, enclosing and isolating a portion of the face of the subject during the delivery of the sample; and
    validity assurance means at least partially housed within said face mask for preventing outside interference during the test and assuring validity of the breath alcohol test wherein the validity assurance means includes means for monitoring the location of the face with respect to the mask.

13. The breath alcohol testing system of claim 12 wherein said validity assurance means further comprises:
    identity confirmation means to confirm the identity of the subject upon successful completion of an identity confirmation test, said identity confirmation means being at least partially housed in the face mask and wherein said validity assurance means assures that the same subject both delivers the breath sample and performs the identity confirmation test.

14. The breath alcohol testing system of claim 13 wherein said identity confirmation means includes voice verification means and said face mask shields said voice verification means from noise generated externally of said face mask when the face is enclosed.

15. The breath alcohol testing system of claim 13 wherein said face mask has an edge that engages the portion of the subject's face, and the identity confirmation means further comprises:
    voice verification means for receiving voiced samples from said subject for comparison with prior recorded samples from said subject to verify the identity of said subject, said voice verification means requiring said voiced samples to emanate from a source closer to said voice verification means than said edge of said face mask in order to verify the identity of said subject.

16. The breath alcohol testing system of claim 13 wherein said validity assurance means further comprises:
    source means directing signals toward the face of said subject when said subject is in the proximity of said face mask;
    detection means for receiving said signals reflected from said subject's face when said subject is in the proximity of said face mask, said face mask being opaque to said signals.

17. The breath alcohol testing system of claim 13 wherein the face mask has an edge that engages the portion of the subject's face and said means for assuring further comprises:
    source means for directing signals toward the face of said subject when said subject is in the proximity of said face mask;
    detecting means for receiving said signals reflected from said subject's face when said subject is in the proximity of said face mask, said source means and said detecting means being oriented such that maximum reflection of said signals from said source means off said subject's face and to said detection means occurs when the edge of said face mask engages and encloses a portion of said subject's face.

18. The breath alcohol testing system of claim 17 wherein said identity confirmation means further comprises voice verification means, including a microphone at least partially housed within the face mask, said microphone oriented with respect to said source means and said detection means such that successful completion of said identity confirmation test requires positioning of the face mask such that maximum reflection of said signal is provided.

19. A breath alcohol testing system particularly suitable for unsupervised blood alcohol testing of a subject comprising:
   a face mask having an internal surface, an external surface and an edge therebetween, said internal surface further defining a breath tube to convey a breath sample to means for testing said sample, said edge shaped for at least partially enclosing a portion of the face of a subject during delivery of said breath sample into said breath tube;
   breath alcohol sensing means at least partially disposed within said face mask and in communication with said breath tube, said face mask ensuring delivery of a deep breath sample into said breath tube by substantially isolating said subject during said delivery of said breath sample; and
   detection means at least partially disposed within said face mask to detect enclosure of a portion of said subject's face and to cause said breath test to be failed if said face mask is withdrawn after said detection of facial enclosure but prior to the delivery of said breath sample.

20. The breath alcohol testing system of claim 19 and further comprising:
   means responsive to the performance of an identity confirming act performed by said subject to verify the identity of said subject, said performance responsive means at least partially disposed within said face mask; and
   said detection means causing said breath test to be failed if said face mask is withdrawn before said subject completes both said delivery and said performance of said identity confirming act.

21. A method for unsupervised breath alcohol testing of a subject comprising the steps of:
   engaging a portion of the face of the subject with a facemask having an internal surface, an external surface and an edge therebetween, the internal surface defining a breath tube to convey the breath sample to means for testing the sample, the edge of the face mask adapted to isolate and enclose said portion of the face;
   monitoring the location of the face of the subject with respect to the mask during engagement; and
   delivering into said face mask a breath sample to be analyzed by a breath sensing apparatus while the portion of the face is engaged.

22. The method for unsupervised breath alcohol testing of claim 21 wherein the face mask has voice analysis apparatus at least partially disposed therein and further comprising the step of:
   speaking voiced samples into said face mask for comparison with prior recorded signals stored in said voice analysis apparatus to provide identity confirmation of the subject.

23. The method for unsupervised breath alcohol testing of claim 21 wherein the face mask has voice analysis apparatus at least partially disposed therein and further comprising the steps of:
   enrolling said subject by eliciting spoken enrollment samples into said face mask to generate and to record in said voice analysis apparatus a reference voice signal correlated to said elicited spoken enrollment samples;
   speaking voiced samples into said face mask for comparison with said prior recorded reference voice signal to enable identity confirmation of said subject.

24. The method for unsupervised breath alcohol testing of claim 21 wherein said face is engaged by said face mask edge during both said speaking step and said delivery step and said face remains engaged continuously in time between said speaking and delivering steps.

25. The method for unsupervised breath alcohol testing of claim 23 wherein said enrolling and said speaking steps are performed when the face is engaged by said face mask edge.

26. A method for unsupervised breath alcohol testing of a breath sample received from a predetermined subject comprising the steps of:
   providing a face mask having an edge adapted to engage and enclose a portion of the face of the subject;
   generating a reference voice signal from enrollment words spoken by said subject into said mask with the edge engaging a portion of the face;
   recording information correlated to said enrollment words;
   comparing said correlated recorded information with a subsequent voiced sample delivered within said face mask;
   confirming the identity of said subject via said comparing step as a necessary condition to the delivery of a breath sample;
   receiving within the face mask a breath sample to be analyzed by a breath sensing apparatus; and
   monitoring the position of said face mask with respect to said subject during delivery of said subsequent voiced samples and during said receiving step and continuously in time therebetween, thereby to insure that the said voiced samples and said breath sample emanate from said subject when the face of said subject is engaged and enclosed by said face mask.

27. The method for unsupervised breath alcohol testing of claim 26 wherein said monitoring step further comprises:
   transmitting signals toward the subject from a source means and receiving said signals after reflection from the subject at a detection means when the portion of the face is engaged by said face mask, said source means and said detection means both being at least partially disposed within said face mask.

* * * * *